United States Patent
Auzely-Velty et al.

(10) Patent No.: US 9,549,987 B2
(45) Date of Patent: Jan. 24, 2017

(54) GLUCOSE RESPONSIVE HYDROGEL COMPRISING PBA-GRAFTED HYALURONIC ACID (HA)

(71) Applicants: CENTRE NATIONAL DE LA RECHERCHE SCIENTIFIQUE (CNRS), Paris (FR); UNIVERSITE JOSEPH FOURIER—GRENOBLE 1, St Martin d'Heres (FR)

(72) Inventors: Rachel Auzely-Velty, Le Gua (FR); Emilie Hachet, La Roche-sur-yon (FR); Bogdan Catargi, Le Bouscat (FR); Valérie Ravaine, Cestas (FR); Léa Messager, Morlaix (FR)

(73) Assignees: CENTRE NATIONAL DE LA RECHERCHE SCIENTIFIQUE (CNRS), Paris (FR); UNIVERSITE JOSEPH FOURIER—GRENOBLE 1, St Martin d'Heres (FR)

( * ) Notice: Subject to any disclaimer, the term of this patent is extended or adjusted under 35 U.S.C. 154(b) by 69 days.

(21) Appl. No.: 14/440,812

(22) PCT Filed: Nov. 6, 2013

(86) PCT No.: PCT/EP2013/073140
§ 371 (c)(1),
(2) Date: May 5, 2015

(87) PCT Pub. No.: WO2014/072330
PCT Pub. Date: May 15, 2014

(65) Prior Publication Data
US 2015/0283247 A1    Oct. 8, 2015

(30) Foreign Application Priority Data
Nov. 6, 2012 (EP) .................... 12306369

(51) Int. Cl.
| | |
|---|---|
| A61K 47/36 | (2006.01) |
| A61K 38/28 | (2006.01) |
| C08B 37/08 | (2006.01) |
| C08L 5/08 | (2006.01) |
| A61K 9/00 | (2006.01) |

(Continued)

(52) U.S. Cl.
CPC ............ *A61K 47/36* (2013.01); *A61K 9/0019* (2013.01); *A61K 9/06* (2013.01); *A61K 38/28* (2013.01); *C08B 37/0072* (2013.01); *C08J 3/075* (2013.01); *C08J 3/24* (2013.01); *C08J 3/243* (2013.01); *C08J 3/28* (2013.01); *C08L 5/08* (2013.01); *A61K 9/5161* (2013.01); *C08J 2305/08* (2013.01); *C08J 2405/08* (2013.01)

(58) Field of Classification Search
CPC ....................................................... A61K 47/36
See application file for complete search history.

(56) References Cited

PUBLICATIONS

Extended European Search Report, issued Jan. 31, 2013, for European Application No. 12306369.5.

(Continued)

*Primary Examiner* — Benjamin Packard
(74) *Attorney, Agent, or Firm* — Birch, Stewart, Kolasch & Birch, LLP

(57) ABSTRACT

Polymer composition comprising a mixture of PBA modified HA polymer grafted on at least a hydroxyl with a group comprising phenylboronic acid and Cis-diol modified HA polymer grafted on at least a hydroxyl with a group comprising a cis-diol. Injectable or implantable glucose-sensitive hydrogels comprising a this polymer composition.

19 Claims, 10 Drawing Sheets

Figure 1:
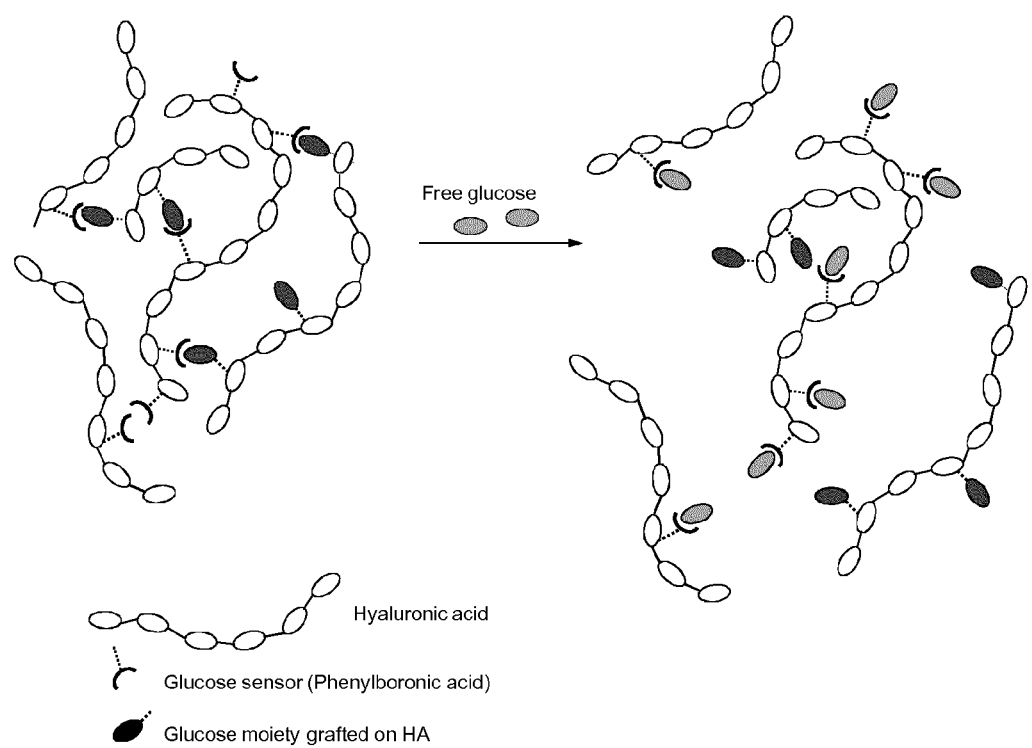

(51) Int. Cl.
    A61K 9/06    (2006.01)
    C08J 3/075   (2006.01)
    C08J 3/24    (2006.01)
    C08J 3/28    (2006.01)
    A61K 9/51    (2006.01)

(56) References Cited

PUBLICATIONS

International Search Report and Written Opinion of the International Search Authority (forms PCT/ISA/210, PCT/ISA/237 and PCT/ISA/220), issued Feb. 27, 2014, for International Application No. PCT/EP2013/073140.

Ivanov et al., "Synthesis of Boronate-containing Copolymers of N,N-dimethylacrylamide, their Interaction with Poly(Vinyl Alcohol) and Rheological Behavior of the Gels," Polymer, vol. 45, 2004, pp. 2495-2505.

Kataoka et al., "Totally Synthetic Polymer Gels Responding to External Glucose Concentration: Their Preparation and Application to On-Off Regulation of Insulin Release," J. Am. Chem. Soc., vol. 120, No. 48, (published on web Nov. 19, 1998), 1998, pp. 12694-12695.

Kitano et al., "A Novel Drug Delivery System Utilizing a Glucose Responsive Polymer Complex Between Poly (Vinyl Alcohol) and Poly (N-vinyl-2-pyrrolidone) with a Phenylboronic Acid Moiety," Journal of Controlled Release, vol. 19, 1992, pp. 161-170.

Matsumoto et al., "Glucose-Responsive Polymer Gel Bearing Phenylborate Derivative as a Glucose-Sensing Moiety Operating at the Physiological pH," Biomacromolecules, vol. 5, No. 3, Published online Apr. 15, 2004, pp. 1038-1045.

Ravaine et al., "Chemically Controlled Closed-loop Insulin Delivery," Journal of Controlled Release, vol. 132, Available online Aug. 23, 2008, pp. 2-11.

Samoei et al., "A Chemomechanical Polymer that Functions in Blood Plasma with High Glucose Selectivity," Angew. Chem. Int. Ed., vol. 45, 2006, pp. 5319-5322.

Wang et al., "A pH-, Thermo-, and Glucose-, Triple-responsive Hydrogels: Synthesis and Controlled Drug Delivery," Reactive & Functional Polymers, vol. 70, Available online Nov. 26, 2009, pp. 159-167.

Wu et al., "Organization of Glucose-Responsive Systems and Their Properties," Chemical Reviews, vol. 111, Sep. 8, 2011, pp. 7855-7875.

Wu et al., "Phenylboronic Acid Grafted Chitosan as a Glucose-Sensitive Vehicle for Controlled Insulin Release," Journal of Pharmaceutical Sciences, vol. 100, No. 6, May, 2011 (Published Online Jan. 25, 2011), pp. 2278-2286.

A)

B)

A)

B)

A)

B)

C)

A)

B)

C)

D)

GLUCOSE RESPONSIVE HYDROGEL COMPRISING PBA-GRAFTED HYALURONIC ACID (HA)

The present invention relates to novel glucose-sensitive hydrogels based on biopolymers, which can be used as insulin delivery systems in the treatment of diabetes and related aspects.

Diabetes mellitus is a disorder of glucose regulation, characterized by an accumulating glucose concentration in the blood. The breakdown of glucose regulation can be attributed to the inability of the endocrine pancreas to secrete insulin or to the body's inability to properly use insulin. In the case of type 1 diabetes, the usual treatment consists in multiple daily blood glucose controls and subcutaneous injections. However, a better control of the glycemia could be achieved if the insulin dose could be continuously adapted to the level of glucose in the blood, therefore avoiding glucose levels below or above the normal range, which causes detrimental complications. In this context, closed-loop delivery of insulin is highly sought-after.

Glucose-responsive polymers and especially hydrogels have attracted much attention in this area due to their ability to both detect the glucose level and deliver insulin accordingly. The variation of the permeability of these highly swollen networks, as a result of their reversible swelling according to blood glucose concentration, makes them suitable for achieving self-regulated insulin delivery.

For this purpose, it is necessary to introduce a glucose sensor moiety on the polymer chain and phenyl boronic acid (PBA) has appeared as an ideal candidate as this molecule is relatively unaffected by unstability and risk of immune response compared to other glucose-recognition elements (glucose oxidase, concanavalin A). Phenylboronic acid is known to reversibly bind to diols to form a cyclic boronic ester in aqueous media (Kataoka et al., 1998). Several research studies have established glucose-responsive polymer gel systems containing PBA (Kataoka et al., 1998; Ravaine et al., 2008; Samoei et al., 2006; Wang et al., 2010; Wu et al., 2011).

However, these glucose responsive systems have a number of drawbacks. The polymers are generally synthetic, non-biodegradable and are not biocompatible, which prevents in vivo applications.

Moreover, the formation of a dynamic matrix comprising boronic acid (PBA) as glucose sensor is based on the formation of boronate-cis-diol complexes which are stable at alkaline pH but not under physiological conditions.

The invention describes a novel biopolymer complex system sensitive to glucose for modulated insulin delivery. This biopolymer complex is obtained by mixing hyaluronic acid (HA) derivatives modified with PBA and maltose. HA is an anionic linear polysaccharide which is ubiquitous in all tissues where it has important structural and biological functions. It is thus biocompatible and can be degraded by enzymes in the organism. In addition, it can be easily produced by bacterial fermentation. As PBA can bind to molecules having cis-diol units, it can form complexes with the sugar units of the HA chain. However, since the structure of the repeating disaccharide unit of HA (consisting of D-glucuronic acid and N-acetyl-D-glucosamine) does not permit efficient complexation with PBA compared to glucose, maltose moieties, which contain a terminal glucose unit, were grafted on HA in order to promote the formation of a dynamic network (i.e. network formed by dynamic covalent cross-links) by combining PBA- and maltose-modified HA (HA-PBA and HA-maltose, respectively) in aqueous solution. This formulation strategy allowed us to obtain dynamic hydrogels exhibiting glucose-sensitivity based on the competitive displacement of HA-maltose from HA-PBA by free glucose. Advantageously, the formation of a dynamic network was observed at physiological pH, which is unusual compared to other boronate-cis-diol complexes which can only stably exist at alkaline pH (Ivanov et al., 2004; Kitano et al., 1992; Matsumoto et al., 2004).

SUMMARY

A first object of the present invention is a polymer composition comprising a mixture of:
a) PBA modified HA polymer grafted on at least a hydroxyl with a group comprising phenylboronic acid, and
b) Cis-diol modified HA polymer grafted on at least a hydroxyl with a group comprising a cis-diol, wherein said cis-diol is selected in the group consisting of: disaccharides, hexoses, uronic acid derivatives of hexoses, hexosamines, N-acetyl derivatives of hexosamines, glycerol and mannitol.

In a first embodiment of the present invention, the polymer composition comprises a mixture of:
a) PBA modified HA polymer grafted on at least a hydroxyl with a group comprising phenylboronic acid, wherein said group is selected in the group consisting of 3-aminophenylboronic acid, 4-aminophenylboronic acid, 4-(aminoethylcarbamoyl)-3-fluorophenylboronic acid and 4-[(2-aminoethyl)carbamoyl]phenylboronic acid, and
b) Cis-diol modified HA polymer grafted on at least a hydroxyl with a group comprising a cis-diol, wherein said cis-diol is selected in the group consisting of: disaccharides, hexoses, uronic acid derivatives of hexoses, hexosamines, N-acetyl derivatives of hexosamines, glycerol, mannitol and sialic acid.

In a second embodiment of the present invention, the polymer composition according to anyone of the preceding claims comprises a mixture of:
a) PBA modified HA polymer grafted on at least a hydroxyl with a group comprising 3-aminophenylboronic acid, and
b) Cis-diol modified HA polymer grafted on at least a hydroxyl with a group comprising maltose.

In the polymer compositions of the present invention, the PBA modified HA polymer is preferably grafted on at least a hydroxyl with a group comprising phenylboronic acid via thiol-ene coupling and the cis-diol modified HA polymer is preferably grafted on at least a hydroxyl with a group comprising a cis-diol via thiol-ene coupling.

In a third embodiment of the present invention, the polymer composition comprises a mixture of:
a) PBA modified HA polymer grafted on at least a hydroxyl with a PBA group of formula (I)

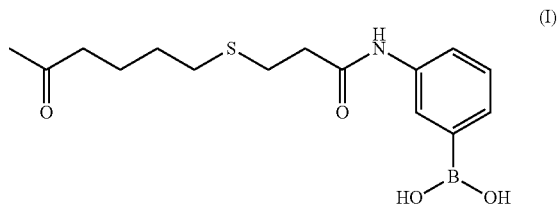 [SMILES: CC(=O)CCCCSCCC(=O)Nc1cccc(B(O)O)c1]

and, b) Cis-diol modified HA polymer grafted on at least a hydroxyl with a maltose group of formula (II)

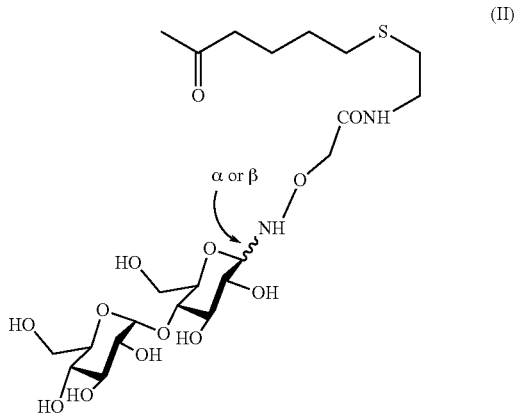

In the polymer compositions of the present invention, the PBA modified HA polymer has preferably a DS with a group comprising phenylboronic acid from 0.02 to 0.6, more preferably from 0.05 to 0.2.

In the polymer compositions of the present invention, the cis-diol modified HA polymer has preferably a DS with a group comprising a cis-diol from 0.02 to 0.6, more preferably from 0.05 to 0.2.

In the polymer compositions of the present invention, the PBA modified HA polymer has preferably a molecular weight $M_w$ from 10 000 g/mol to 3 000 000 g/mol, more preferentially from 20 000 g/mol to 800 000 g/mol and the cis-diol modified HA polymer has a molecular weight $M_w$ from 10 000 g/mol to 3 000 000 g/mol, more preferentially from 20 000 g/mol to 800 000 g/mol.

In the polymer compositions of the present invention, the molar ratio between the group comprising phenylboronic acid and the group comprising a cis-diol is preferably from 0.25/1 to 2.5/1, more preferably from 0.5/1 to 2/1.

In the polymer compositions of the present invention, the composition has preferably a pH from 7 to 10, preferably from 7 to 7.5.

In the polymer compositions of the present invention, the PBA modified HA polymer is preferably further grafted on at least a hydroxyl with an alkene group and the cis-diol modified HA polymer is preferably further grafted on at least a hydroxyl with an alkene group.

In the polymer compositions of the present invention, the alkene group is preferably selected in the group consisting of pentenoate and maleimide.

In the polymer compositions of the present invention, the PBA modified HA polymer has preferably a DS with the alkene group from 0.02 to 0.6, more preferably from 0.05 to 0.5 and the cis-diol modified HA polymer has preferably a DS with the alkene group from 0.02 to 0.6, more preferably from 0.05 to 0.5.

In preferred embodiments of the present invention, the PBA modified HA polymer and the cis-diol modified HA polymer are reversibly covalently crosslinked via their groups comprising phenyl boronic acid and their groups comprising a cis-diol.

In some embodiments, the PBA modified HA polymer and the cis-diol modified HA polymer are chemically crosslinked via their alkene groups. Preferably, the PBA modified HA polymer and the cis-diol modified HA polymer are chemically crosslinked via their alkene groups by a photo-crosslinking reaction with bisthiolated poly(ethylene glycol) $P(EG-(SH)_2)$.

Preferably, the PBA modified HA polymer and the cis-diol modified HA polymer are further reversibly covalently crosslinked via their groups comprising phenyl boronic acid and their groups comprising a cis-diol.

Another object of the present invention is an injectable hydrogel comprising a polymer composition wherein the PBA modified HA polymer and the cis-diol modified HA polymer are reversibly covalently crosslinked via their groups comprising phenyl boronic acid and their groups comprising a cis-diol.

Another object of the present invention is an implantable hydrogel comprising a polymer composition wherein the PBA modified HA polymer and the cis-diol modified HA polymer are chemically crosslinked via their alkene groups and are further reversibly covalently crosslinked via their groups comprising phenyl boronic acid and their groups comprising a cis-diol.

Another object of the present invention is a polymer composition comprising a mixture of:

a) PBA modified HA polymer of formula (III)

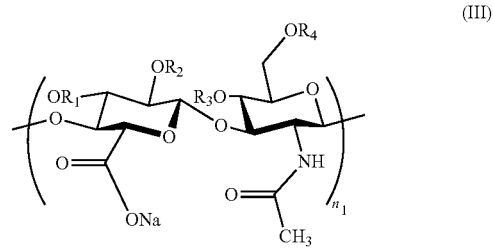

wherein $R_1$, $R_2$, $R_3$ and $R_4$ are independently selected in the group consisting of H, the PBA group of formula (I)

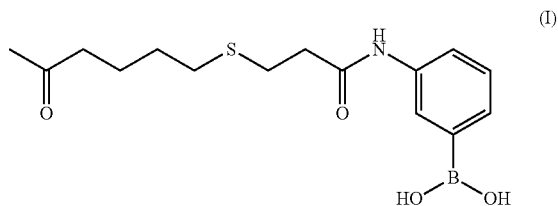 [SMILES: CC(=O)CCCCSCCC(=O)Nc1cccc(B(O)O)c1]

and the alkene group of formula (IV)

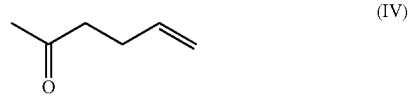

$n_1$ is an integer from 25 to 8000, preferably from 50 to 2000, the DS with the PBA group of formula (I) is from 0.02 to 0.6, preferably from 0.05 to 0.2, the DS with the alkene group of formula (IV) is from 0 to 0.6, preferably from 0.02 to 0.6, and Cis-diol modified HA polymer of formula (V)

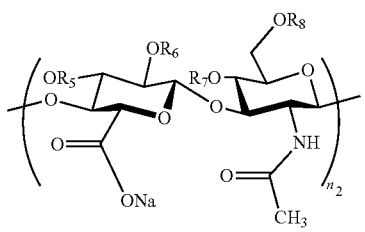

wherein $R_5$, $R_6$, $R_7$ and $R_8$ are independently selected in the group consisting of H, the maltose group of formula (II)

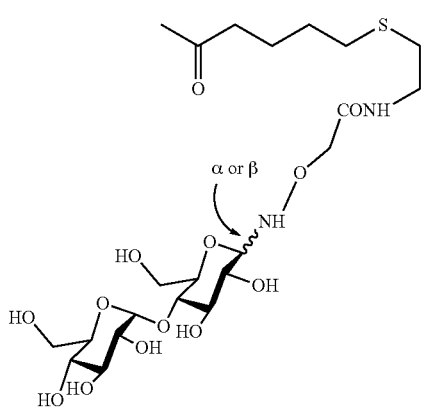

and the alkene group of formula (IV)

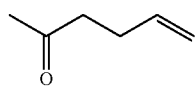

$n_2$ is an integer from 25 to 8000, preferably from 50 to 2000, the DS with the maltose group is from 0.02 to 0.6, preferably from 0.05 to 0.2,
the DS with the alkene group is from 0 to 0.6, preferably from 0.02 to 0.6.

In the present invention the polymer composition comprises preferably a mixture wherein the molar ratio between the PBA group and the alkene group is from 0.25/1 to 2.5/1, preferably from 0.5/1 to 2/1.

In the present invention, the polymer composition preferably has a pH from 7 to 10, preferably from 7 to 7.5.

In the polymer compositions present invention, the PBA modified HA polymer and the cis-diol modified HA polymer are preferably reversibly covalently crosslinked via respectively their PBA groups and their maltose groups.

In the polymer of the present invention, the PBA modified HA polymer has preferably a DS with the alkene group from 0.02 to 0.6, more preferably from 0.05 to 0.2 and the cis-diol modified HA polymer has preferably a DS with the alkene group from 0.02 to 0.6, preferably from 0.05 to 0.2.

In the polymer composition of the present invention, the PBA modified HA polymer and the cis-diol modified HA polymer are preferably chemically crosslinked via their alkene groups. Preferably, the PBA modified HA polymer and the cis-diol modified HA polymer are chemically crosslinked via their alkene groups by a photocrosslinking reaction with PEG-(SH)$_2$. Preferably, the PBA modified HA polymer and the cis-diol modified HA polymer are further reversibly covalently crosslinked via their PBA groups and their maltose groups.

Another object of the present invention is an injectable hydrogel comprising a polymer composition wherein the PBA modified HA polymer and the cis-diol modified HA polymer are reversibly covalently crosslinked via their groups comprising phenyl boronic acid and their groups comprising a cis-diol.

Another object of the present invention is an implantable hydrogel comprising a polymer composition wherein the PBA modified HA polymer and the cis-diol modified HA polymer are chemically crosslinked via their alkene groups and are further reversibly covalently crosslinked via their groups comprising phenyl boronic acid and their groups comprising a cis-diol.

Another object of the present invention is a drug delivery system comprising a polymer composition as described above and a drug contained in said polymer composition. Preferably, the drug delivery system according to the present invention is for use as a medicament. Preferably, the drug delivery system according to the present invention is for use in a method of treatment of diabetes mellitus. In preferred embodiments, the drug is insulin.

Another object of the present invention is a process for manufacturing a PBA modified HA polymer grafted on at least a hydroxyl with a group comprising phenylboronic acid comprising the steps of:
 a) Grafting an alkene group to a hydroxyl of a HA polymer to obtain a HA intermediate modified with alkene groups,
 b) Grafting a thiol group to the group comprising phenylboronic acid to obtain a phenylboronic acid-thiol derivative,
 c) Reacting the product obtained in step a) with the product obtained in step b) to form thioether linkages.

Preferably, in step a) the alkene group is selected from pentenoate and maleimide.

Preferably, in step b) the phenylboronic acid-thiol derivative obtained is the compound of formula (VI)

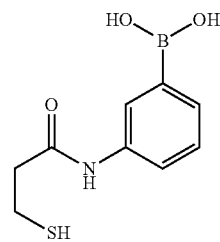

Another object of the present invention is a process for manufacturing a cis-diol modified HA polymer grafted on at least a hydroxyl with a group comprising a cis-diol comprising the steps of:
 a) Grafting an alkene group to a hydroxyl of a HA polymer to obtain a HA intermediate modified with alkene groups,
 b) Grafting a thiol group to the cis-diol to obtain a thiol cis-diol,
 c) Reacting the product obtained in step a) with the product obtained in step b) to form thioether linkages.

Preferably, in step a) the alkene group is selected from pentenoate and maleimide.

Preferably in step b) the cis-diol is maltose and the thiol cis-diol obtained is the compound of formula (VII)

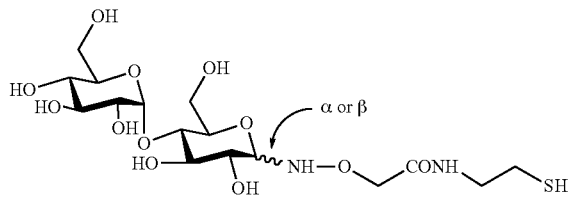

(VII)

Another object of the present invention is a process for manufacturing a reversibly crosslinked hydrogel comprising a HA polymer composition comprising the steps of:
a) Preparing a PBA modified HA polymer grafted on at least a hydroxyl with a group comprising phenylboronic acid;
b) Preparing a cis-diol modified HA polymer grafted on a hydroxyl with a group comprising a cis-diol, wherein said cis-diol is selected in the group consisting of: disaccharides, hexoses, uronic acid derivatives of hexoses, hexosamines, N-acetyl derivatives of hexosamines, glycerol, mannitol and sialic acid;
c) Mixing aqueous solutions of the PBA modified HA polymer of step a) and of the cis-diol modified HA polymer of step at a pH from comprised between 7 and 10, preferably between, 7.2 and 9.5 to obtain a reversibly crosslinked hydrogel.

Another object of the present invention is a process for manufacturing a reversibly crosslinked hydrogel comprising a HA polymer composition comprising the steps of:
a) Preparing a PBA modified HA polymer grafted on at least a hydroxyl with a group comprising phenylboronic acid, wherein said group is selected in the group consisting of phenylboronic acid, 3-aminophenylboronic acid, 4-aminophenylboronic acid, 4-(aminoethylcarbamoyl)-3-fluorophenylboronic acid and 4-[(2-aminoethyl)carbamoyl]phenylboronic acid;
b) Preparing a cis-diol modified HA polymer grafted on a hydroxyl with a group comprising a cis-diol, wherein said cis-diol is selected in the group consisting of: disaccharides, hexoses, uronic acid derivatives of hexoses, hexosamines, N-acetyl derivatives of hexosamines, glycerol, mannitol and sialic acid;
c) Mixing aqueous solutions of the PBA modified HA polymer of step a) and of the cis-diol modified HA polymer of step b) at a pH comprised between 7 and 10, preferably between, 7.2 and 9.5 to obtain a reversibly crosslinked hydrogel.

Preferably, in step c) mixing aqueous solutions of the PBA modified HA polymer of step a) and of the cis-diol HA polymer of step b) is performed in the presence of a drug thereby incorporating the drug into the HA polymer composition.

Another object of the present invention is a process for manufacturing a double cross-linked hydrogel comprising a HA polymer composition comprising the steps of:
a) Preparing a PBA modified HA polymer grafted on at least a hydroxyl with a group comprising phenylboronic acid, wherein said group is selected in the group consisting of phenylboronic acid, 3-aminophenylboronic acid, 4-aminophenylboronic acid, 4-(aminoethylcarbamoyl)-3-fluorophenylboronic acid and 4-[(2-aminoethyl)carbamoyl]phenylboronic acid, and grafted on at least a hydroxyl with an alkene group;
b) Preparing a cis-diol modified HA polymer grafted on a hydroxyl with a group comprising a cis-diol, wherein said cis-diol is selected in the group consisting of: disaccharides, hexoses, uronic acid derivatives of hexoses, hexosamines, N-acetyl derivatives of hexosamines, glycerol, mannitol and sialic acid, and grafted on at least a hydroxyl with an alkene group;
c) Mixing aqueous solutions of the PBA modified HA polymer of step a) and of the cis-diol modified HA polymer of step b) at a pH from 3 to 6.5 to obtain a HA polymer composition;
d) Photocrosslinking of the HA polymer composition obtained in step c) by the radical addition of PEG-$(SH)_2$ on the alkene groups on the HA polymer composition to obtain a chemically crosslinked HA polymer composition;
e) Crosslinking of the HA polymer composition of step d) at a pH comprised between 7 and 10, preferentially between 7.2 and 9.5.

In preferred embodiments, after step d) a drug is incorporated into the HA polymer composition.

DETAILED DESCRIPTION OF THE INVENTION

The present invention describes polymer compositions obtained by mixing HA derivatives modified with PBA (phenylboronic acid) and HA derivatives modified with a cis-diol.

By crosslinking of these hydrophilic HA polymers a network of polymer chains is obtained resulting in the formation of an hydrogel which is highly water absorbent.

More particularly, at a pH ranging from 7 to 10, crosslinking of HA molecules by boronate-cis-diol complexes occurs and the compositions of the present invention form a dynamic matrix or hydrogel. Surprisingly, the boronate-cis-diol complexes which are usually only stable at alkaline pH exhibit remarkable stability at lower pH including at physiological pH (7.4).

These compositions form dynamic hydrogels exhibiting glucose-sensitive viscosity based on the competitive displacement of cis-diol modified HA from PBA modified HA by free glucose.

The hydrogels of the present invention can have properties ranging from soft to hard rendering them suitable both for injection or implantation.

In the present invention, the term "HA" refers to sodium hyaluronate, hyaluronan, hyaluronic acid or hyaluronate and in particular to hyaluronan having CAS number 9004-61-9 and 9067-32-7 (sodium salt).

The HA glycosaminoglycan may be represented by the following formula:

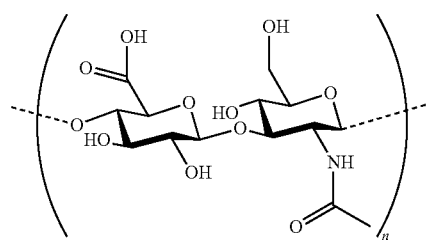

The compositions of the present invention comprise a PBA modified HA polymer grafted on at least a hydroxyl with a group comprising phenylboronic acid and a cis-diol modified HA polymer grafted on at least a hydroxyl with a group comprising a cis-diol. The PBA modified HA and the cis-diol modified HA may comprise any other functional group grafted in particular on the hydroxyl groups of the HA polymer.

Typically, the polymer compositions of the present invention are obtained by mixing aqueous solutions of PBA modified HA and cis-diol modified HA. At a pH from 7 to 10, more preferably from 7.2 to 9.5, a dynamic hydrogel is formed comprising boronate-cis-diol complexes crosslinking the HA molecules. The boronate-cis-diol complexes are sensitive to glucose and accordingly the swelling, viscosity and permeability of the hydrogels of the present invention will vary depending on the presence of glucose and the amount of glucose present in the medium.

The compositions and hydrogels of the present invention are glucose-sensitive. Any drug or API (active pharmaceutical ingredient) may be incorporated into the compositions and hydrogels of the present invention. The compositions and hydrogels of the present invention can be used as drug delivery systems wherein release of a drug from the hydrogel is regulated by glucose concentration.

A first object of the present invention is a polymer composition comprising a mixture of:
a) PBA modified HA polymer grafted on at least a hydroxyl with a group comprising phenylboronic acid, and
b) Cis-diol modified HA polymer grafted on at least a hydroxyl with a group comprising a cis-diol.

In the present invention, the group comprising phenylboronic acid (PBA) may be any group comprising PBA or a PBA derivative able to form boronate-cis-diol complexes with the group comprising a cis-diol.

In the present invention, the group comprising a cis-diol is preferably selected in the group consisting of:
disaccharides such as maltose, lactose and sucrose;
hexoses such as glucose, galactose and mannose;
uronic acid derivatives of hexoses such as glucuronic acid, galacturonic acid, and mannuronic acid;
hexosamines such as galactosamine and glucosamine;
N-acetyl derivatives of hexosamines such as N-acetylgalactosamine and N-acetylglucosamine;
glycerol;
mannitol; and
sialic acid.

In a first embodiment of the present invention, the polymer composition comprises a mixture of:
a) PBA modified HA polymer grafted on at least a hydroxyl with a group comprising phenylboronic acid, wherein said group is selected in the group consisting of phenylboronic acid, 3-aminophenylboronic acid, 4-aminophenylboronic acid, 4-(aminoethylcarbamoyl)-3-fluorophenylboronic acid and 4-[(2-aminoethyl)carbamoyl]phenylboronic acid, and
b) Cis-diol modified HA polymer grafted on at least a hydroxyl with a group comprising a cis-diol, wherein said cis-diol is selected in the group consisting of: disaccharides, hexoses, uronic acid derivatives of hexoses, hexosamines, N-acetyl derivatives of hexosamines, glycerol, mannitoland sialic acid.

In a second embodiment of the present invention, the polymer composition comprises a mixture of:

a) PBA modified HA polymer grafted on at least a hydroxyl with a group comprising 3-aminophenylboronic acid, and
b) Cis-diol modified HA polymer grafted on at least a hydroxyl with a group comprising maltose.

In a third embodiment of the present invention, the polymer composition comprises a mixture of:
a) PBA modified HA polymer grafted on at least a hydroxyl with a PBA group of formula (I)

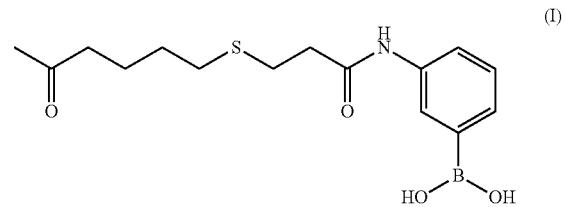 [SMILES: CC(=O)CCCCSCCC(=O)Nc1cccc(B(O)O)c1]

and,
b) Cis-diol modified HA polymer grafted on at least a hydroxyl with a maltose group of formula (II)

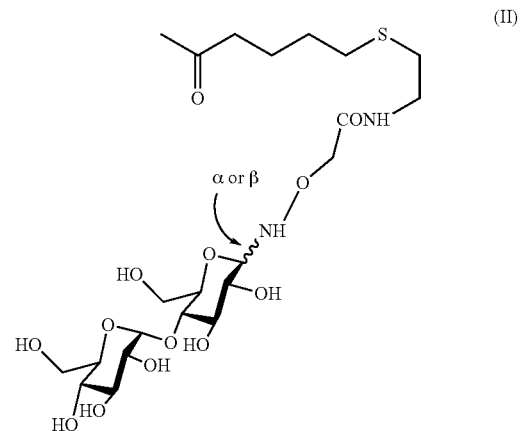

In the polymer compositions of the present invention, the PBA modified HA polymer is preferably grafted on at least a hydroxyl with a group comprising phenylboronic acid via thiol-ene coupling and the cis-diol modified HA polymer is preferably grafted on at least a hydroxyl with a group comprising a cis-diol via thiol-ene coupling.

The synthetic strategy based on thiol-ene coupling developed by the inventors provides PBA modified HA and cis-diol modified HA with varying degrees of substitution. In view of this synthetic strategy, these HA polymers may also possess alkene groups grafted on the hydroxyl groups along the polymer chain. These alkene groups may be advantageously used to chemically crosslink the glucose-sensitive hydrogels of the present invention. The alkene groups may further be used for further functionalization of the HA polymer. This synthetic strategy is also described in WO2012/066133.

In the polymer compositions of the present invention, the PBA modified HA polymer is preferably further grafted on at least a hydroxyl with an alkene group and the cis-diol modified HA polymer is preferably further grafted on at least a hydroxyl with an alkene group.

In the polymer compositions of the present invention, the alkene group is preferably selected in the group consisting of pentenoate and maleimide.

In the polymer compositions of the present invention, the PBA modified HA polymer has preferably a DS with the alkene group from 0.02 to 0.6, more preferably from 0.05 to 0.5 and the cis-diol modified HA polymer has preferably a DS with the alkene group from 0.02 to 0.6, more preferably from 0.05 to 0.5.

Any other method may be used to graft PBA groups or cis-diol groups along the HA chain via the hydroxyl groups of the polymer.

In a fourth embodiment of the present invention, the polymer composition comprises a mixture of:

a) PBA modified HA polymer of formula (III)

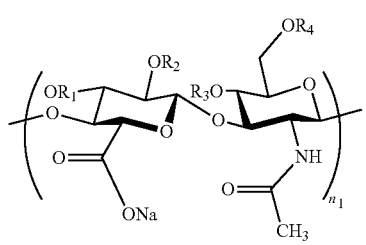
(III)

wherein $R_1$, $R_2$, $R_3$ and $R_4$ are independently selected in the group consisting of H, the PBA group of formula (I)

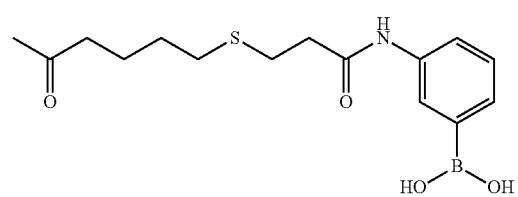
(I)

and the alkene group of formula (IV)

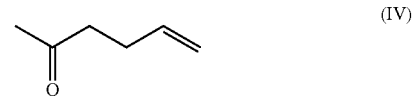
(IV)

$n_1$ is an integer from 25 to 8000, preferably from 50 to 2000, the DS with the PBA group of formula (I) is from 0.02 to 0.6, preferably from 0.05 to 0.2,
the DS with the alkene group of formula (IV) is from 0 to 0.6, preferably from 0.02 to 0.6, and b) Cis-diol modified HA polymer of formula (V)

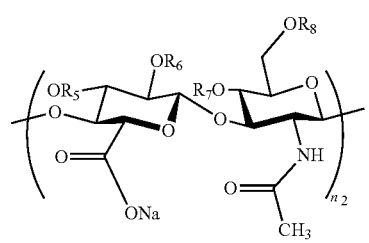
(V)

wherein $R_5$, $R_6$, $R_7$ and $R_8$ are independently selected in the group consisting of H, the maltose group of formula (II)

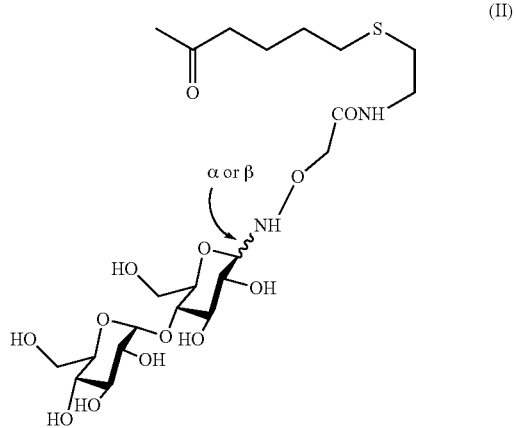
(II)

and the alkene group of formula (IV)

(IV)

$n_2$ is an integer from 25 to 8000, preferably from 50 to 2000, the DS with the maltose group is from 0.02 to 0.6, preferably from 0.05 to 0.2,
the DS with the alkene group is from 0 to 0.6, preferably from 0.02 to 0.6.

In the polymer compositions of the present invention, the PBA modified HA polymer has preferably a DS with a group comprising phenylboronic acid from 0.02 to 0.6, more preferably from 0.05 to 0.2.

In the polymer compositions of the present invention, the cis-diol modified HA polymer has preferably a DS with a group comprising a cis-diol from 0.02 to 0.6, more preferably from 0.05 to 0.2.

In the polymer compositions of the present invention, the PBA modified HA polymer has preferably a DS with an alkene group from 0.02 to 0.6, more preferably from 0.05 to 0.5 and the cis-diol modified HA polymer has preferably a DS with an alkene group from 0.02 to 0.6, more preferably from 0.05 to 0.5.

In the polymer compositions of the present invention, the alkene group is preferably selected in the group consisting of pentenoate and maleimide.

In the polymer compositions of the present invention, the PBA modified HA polymer has preferably a molecular weight $M_w$ from 10 000 g/mol to 3 000 000 g/mol, more preferentially from 20 000 g/mol to 800 000 g/mol and the cis-diol modified HA polymer has a molecular weight $M_w$ from 10 000 g/mol to 3 000 000 g/mol, more preferentially from 20 000 g/mol to 800 000 g/mol.

In the polymer compositions of the present invention, the molar ratio between the group comprising phenylboronic acid and the group comprising a cis-diol is preferably from 0.25/1 to 2.5/1, more preferably from 0.5/1 to 2/1.

The polymer compositions of the present invention preferably have a pH from 7 to 10, preferably from 7.2 to 9.5, more preferably from 7.2 to 7.5 and even more preferably of 7.4 (physiological pH).

The compositions of the present invention form cross-linked hydrogels at neutral or alkaline pH. The PBA modified HA polymer and the cis-diol modified HA polymer are reversibly covalently crosslinked via their groups comprising phenyl boronic acid and their groups comprising a cis-diol. This crosslinking is "dynamic" or "reversible" as it will vary in response to glucose.

The swelling, viscosity and permeability of these dynamic hydrogels also depend on the DS with the PBA group or the cis-diol group for each of the modified HA polymers of the composition. The molar ratio between the group comprising phenylboronic acid and the group comprising a cis-diol in the polymer composition also determines the properties of the HA hydrogel as well as the Mw of the HA polymers.

Hydrogels with tunable glucose-sensitivity are obtained by changing these different parameters.

Drugs, APIs or any other active ingredient may be incorporated into the hydrogels before or during reversible crosslinking of the HA polymer by formation of boronate-cis diol complexes.

The hydrogels obtained by crosslinking the PBA groups and the cis-diol group of the HA polymers via formation of boronate-cis diol complexes may in particular be used as injectable hydrogels.

These hydrogels may also be formulated as nanoparticles having a size comprised between 50 and 1000 nm, preferably between 100 and 500 nm. These nanoparticles are also suitable for administration by injection.

Therefore, another object of the present invention is an injectable hydrogel comprising a polymer composition wherein the PBA modified HA polymer and the cis-diol modified HA polymer are reversibly covalently crosslinked via their groups comprising phenyl boronic acid and their groups comprising a cis-diol.

The polymer compositions of the present invention may further be chemically crosslinked by any appropriate method known to the skilled person.

In the present invention, chemical crosslinking of the HA polymer composition may be performed via the alkene groups grafted on the hydroxyls along the HA polymer chains. In these embodiments, the PBA modified HA polymer and the cis-diol modified HA polymer are chemically crosslinked via their alkene groups.

The PBA modified HA and the cis-diol modified HA may further be chemically crosslinked via their alkene groups by any method known to the skilled person. In preferred embodiments, formation of chemically crosslinked hydrogels is performed by radical-thiol ene addition reactions. Preferably, the PBA modified HA polymer and the cis-diol modified HA polymer are chemically crosslinked via their alkene groups by a photocrosslinking reaction with bisthiolated poly(ethylene glycol) (PEG-(SH)$_2$).

After the chemical crosslinking, a drug, an API or any active ingredient may be incorporated into the hydrogel before the reversible and dynamic glucose-sensitive crosslinking is carried out via the PBA groups and the cis-diol groups along the HA polymer chains.

Preferably, the chemically crosslinked hydrogels comprising the PBA modified HA polymer and the cis-diol modified HA polymer are further reversibly covalently crosslinked via their groups comprising phenyl boronic acid and their groups comprising a cis-diol.

These double crosslinked hydrogels, comprising a polymer composition wherein the PBA modified HA polymer and the cis-diol modified HA polymer are chemically crosslinked via their alkene groups and are further reversibly covalently crosslinked via their groups comprising phenyl boronic acid and their groups comprising a cis-diol, may in particular be used as implantable hydrogels.

The double crosslinked hydrogels of the present invention may also be formulated as nanoparticles having a size comprised between 50 and 1000 nm, preferably between 100 and 500 nm. These nanoparticles are suitable for administration by injection.

Another object of the present invention is an implantable hydrogel comprising a polymer composition wherein the PBA modified HA polymer and the cis-diol modified HA polymer are chemically crosslinked via their alkene groups and are further reversibly covalently crosslinked via their groups comprising phenyl boronic acid and their groups comprising a cis-diol.

Another object of the present invention is a drug delivery system comprising a polymer composition as described above and a drug or active ingredient contained in said polymer composition. The drug delivery systems of the present invention provide glucose-sensitive release of drugs or active ingredients. Preferably, the drug delivery system according to the present invention is for use as a medicament. Preferably, the drug delivery system according to the present invention is for use in a method of treatment of diabetes mellitus. In preferred embodiments, the drug is insulin.

To prepare the hydrogels of the present invention in a versatile manner, the inventors developed a synthetic strategy allowing the synthesis of PBA modified HA and cis-diol modified HA with varying degrees of substitution. The hydrogel behavior was quantified by measuring the dynamic rheology of HA-PBA/HA-cis-diol mixtures in aqueous solutions, without and in the presence of free glucose. Notably, we showed that the type of glucose response is strongly affected by changing ratios between HA-bound PBA and HA-bound cis-diol, which can be advantageously used to precisely tune glucose-sensitivity and to control tightly the release of a drug from the hydrogels. Based on these considerations an aspect of the invention relates to the development of dynamic hydrogels with tunable glucose-sensitivity, from chemically modified biocompatible and biodegradable natural polysaccharides. Another aspect of this invention relates to the development of a versatile route to polysaccharides derivatives possessing either PBA groups or cis-diol moieties along the chain with varying degree of substitution (DS). Notably, depending on the DS, these polysaccharides can also possess alkene groups along the chain which can be used to chemically crosslink the glucose sensitive networks. The resulting chemical hydrogels can be used as implantable materials for achieving for example self-regulated insulin delivery as a result of their reversible swelling according to blood glucose concentration.

The HA derivatives were synthesized from a common intermediate possessing alkene functionalities along the chain as illustrated in Scheme 1.

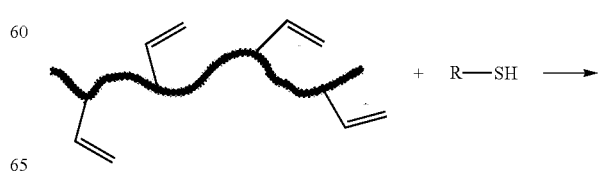

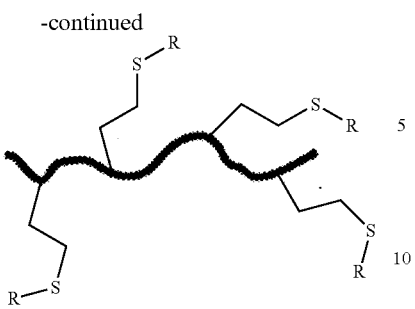

R—SH: Cis-diol derivative or phenylboronic acid derivative functionalized by a thiol group Scheme 1: Synthetic Strategy for the Grafting of Phenylboronic Acid and Maltose Moieties on HA Based on Thiol-Ene Reactions The strategy for the functionalization of HA with PBA and cis-diol relies on a "thiol-ene reaction", which has been classified as click chemistry because of its simplicity, high reactivity, and the broad variety of available reagents. The thiol-ene reaction is based on the radical addition of thiols on double bonds resulting in the formation of thioether linkages. In order to be reacted with functional thiols, HA was first functionalized with alkene groups according to a procedure previously described in WO2012/066133. We indeed developed mild conditions to functionalize HA with alkene groups by reaction of the polysaccharide with carboxylic acid anhydride in hydroorganic media. The degree of substitution of HA-alkene can be adjusted by varying the [carboxylic acid anhydride]/[HA] feed ratio. For example, using a [pentenoic acid anhydride]/[HA] ratio of 1, we obtained a pentenoate-modified HA with a DS of 0.2 which was further reacted in thiol-ene reactions with cis-diol-thiol and PBA-thiol derivatives.

Accordingly, another object of the present invention is a process for manufacturing a PBA modified HA polymer grafted on at least a hydroxyl with a group comprising phenylboronic acid comprising the steps of:
a) Grafting an alkene group to a hydroxyl of a HA polymer to obtain a HA intermediate modified with alkene groups,
b) Grafting a thiol group to the group comprising phenylboronic acid to obtain a phenylboronic acid-thiol derivative,
c) Reacting the product obtained in step a) with the product obtained in step b) to form thioether linkages.

Preferably, in step a) the alkene group is selected from pentenoate and maleimide.

Preferably, in step b) the phenylboronic acid-thiol derivative obtained is the compound of formula (VI)

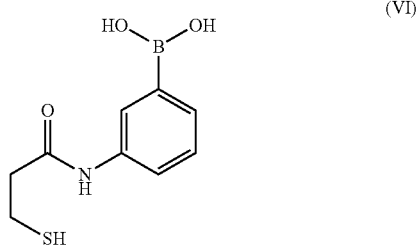 [SMILES: O=C(CCS)Nc1cccc(B(O)O)c1]

(VI)

Another object of the present invention is a process for manufacturing a cis-diol modified HA polymer grafted on at least a hydroxyl with a group comprising a cis-diol comprising the steps of:
a) Grafting an alkene group to a hydroxyl of a HA polymer to obtain a HA intermediate modified with alkene groups,
b) Grafting a thiol group to the cis-diol to obtain a thiol cis-diol,
c) Reacting the product obtained in step a) with the product obtained in step b) to form thioether linkages.

Preferably, in step a) the alkene group is selected from pentenoate and maleimide.

Preferably in step b) the cis-diol is maltose and the thiol cis-diol obtained is the compound of formula (VII)

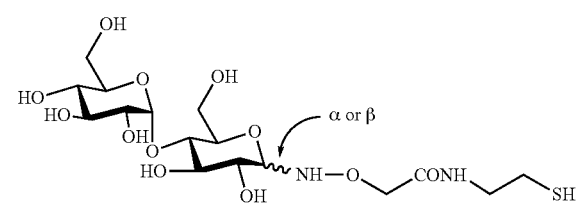

(VII)

Another object of the present invention is a process for manufacturing a dynamically and/or reversibly crosslinked hydrogel comprising a HA polymer composition comprising the steps of:
a) Preparing a PBA modified HA polymer grafted on at least a hydroxyl with a group comprising phenylboronic acid;
b) Preparing a cis-diol modified HA polymer grafted on a hydroxyl with a group comprising a cis-diol;
c) Mixing aqueous solutions of the PBA modified HA polymer of step a) and of the cis-diol modified HA polymer of step b) at a pH comprised between 7 and 10, preferentially between 7.2 and 9.5 to obtain a dynamically and/or reversibly crosslinked hydrogel.

Another object of the present invention is a process for manufacturing a reversibly crosslinked hydrogel comprising a HA polymer composition comprising the steps of:
a) Preparing a PBA modified HA polymer grafted on at least a hydroxyl with a group comprising phenylboronic acid, wherein said group is selected in the group consisting of phenylboronic acid, 3-aminophenylboronic acid, 4-aminophenylboronic acid, 4-(aminoethylcarbamoyl)-3-fluorophenylboronic acid and 4-[(2-aminoethyl)carbamoyl]phenylboronic acid;
b) Preparing a cis-diol modified HA polymer grafted on a hydroxyl with a group comprising a cis-diol, wherein said cis-diol is selected in the group consisting of: disaccharides, hexoses, uronic acid derivatives of hexoses, hexosamines, N-acetyl derivatives of hexosamines, glycerol, mannitol and sialic acid;
c) Mixing aqueous solutions of the PBA modified HA polymer of step a) and of the cis-diol modified HA polymer of step b) at a pH comprised between 7 and 10, preferentially between 7.2 and 9.5 to obtain a reversibly crosslinked hydrogel.

Before or during the reversible/dynamic glucose-sensitive crosslinking of the hydrogels, a drug or any other active ingredient may be incorporated into the hydrogel by any appropriate method. Before the crosslinking step, the drug or active ingredient is typically added to the aqueous solution containing the HA polymer composition and diffuses into the composition or is mixed into the HA composition. Alternatively, the drug may be added to the HA composition during the reversible crosslinking step.

In a preferred embodiment, in step c) mixing aqueous solutions of the PBA modified HA polymer of step a) and of the cis-diol HA polymer of step b) is performed in the presence of a drug thereby incorporating the drug into the HA polymer composition.

Another object of the present invention is a process for manufacturing a double cross-linked hydrogel comprising a HA polymer composition comprising the steps of:
a) Preparing a PBA modified HA polymer
  grafted on at least a hydroxyl with a group comprising phenylboronic acid, wherein said group is selected in the group consisting of phenylboronic acid, 3-aminophenylboronic, 4-aminophenylboronic acid, 4-(aminoethylcarbamoyl)-3-fluorophenylboronic acid and 4-[(2-aminoethyl)carbamoyl]phenylboronic acid, and
  grafted on at least a hydroxyl with an alkene group;
b) Preparing a cis-diol modified HA polymer
  grafted on a hydroxyl with a group comprising a cis-diol, wherein said cis-diol is selected in the group consisting of: disaccharides, hexoses, uronic acid derivatives of hexoses, hexosamines, N-acetyl derivatives of hexosamines, glycerol, mannitol and sialic acid, and
  grafted on at least a hydroxyl with an alkene group;
c) Mixing aqueous solutions of the PBA modified HA polymer of step a) and of the cis-diol modified HA polymer of step b) at a pH from 3 to 6.5 to obtain a HA polymer composition;
d) Photocrosslinking of the HA polymer composition obtained in step c) by the radical addition of PEG-$(SH)_2$ on the alkene groups on the HA polymer composition to obtain a chemically crosslinked HA polymer composition;
e) Crosslinking of the HA polymer composition of step d) at a pH comprised between 7 and 10, preferentially between 7.2 and 9.5.

Step d) is the chemical crosslinking step whereas step e) corresponds to the dynamic or reversible crosslinking step obtained by formation of boronate-cis-diol complexes. As described above, this second crosslinking step is dynamic or reversible and is sensitive to glucose concentration.

After the chemical crosslinking of the HA composition and before or during the dynamic glucose-sensitive crosslinking of the hydrogels, a drug or any other active ingredient may be incorporated into the hydrogel by any appropriate method. The drug or active ingredient is typically added to the aqueous solution containing the HA polymer composition and diffuses into the composition or is mixed into the HA composition.

After the chemical crosslinking step, the HA composition may be immersed in a solution containing a drug or active ingredient of interest to allow for diffusion of the drug into the HA composition. Alternatively, the drug or active ingredient may be directly added to the HA composition at a pH comprised between 7 and 10, preferentially between 7.2 and 9.5 during the reversible crosslinking step.

FIGURES

FIG. 1: Glucose-sensitive hydrogel based on the reversible complexation of phenylboronic acid and maltose moieties grafted on polysaccharide (HA) chains.

Figure 2:
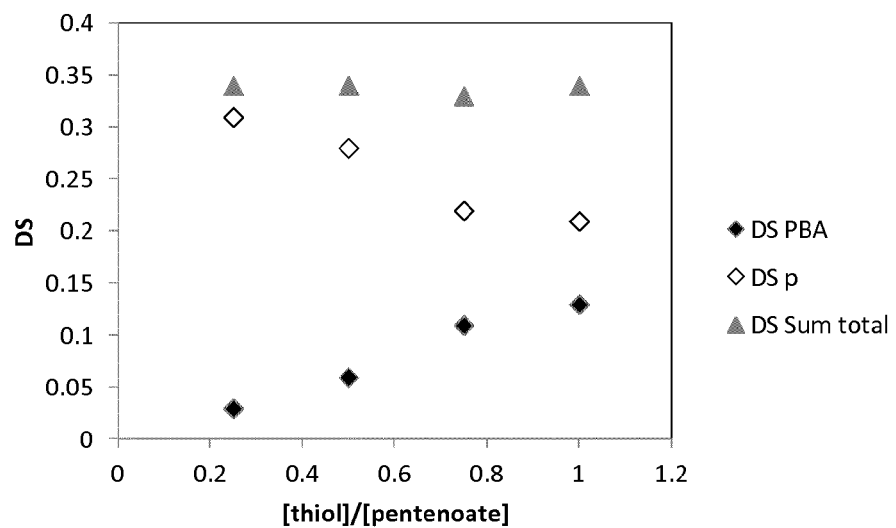
Figure 2:
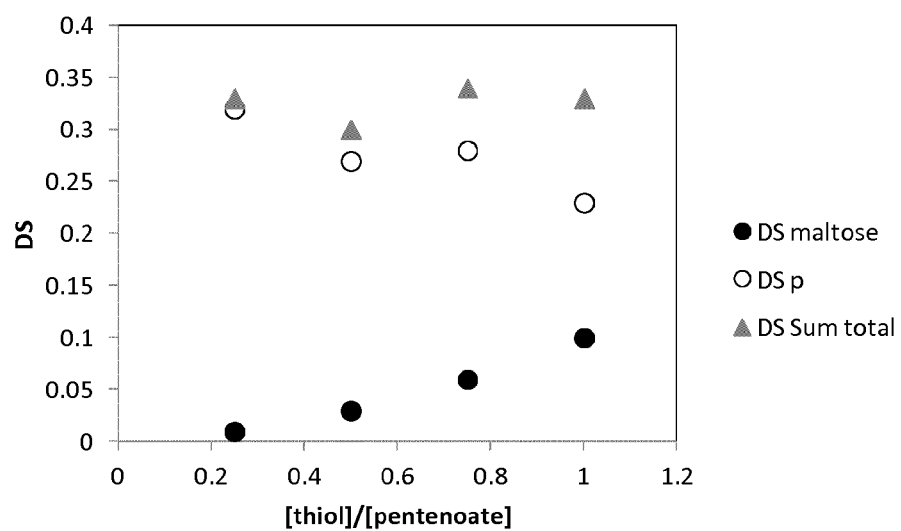

FIG. 2: Synthesis of PBA- and maltose-modified HA. A) Variation of the DS in pentenoates and in PBA groups of HA-PBA as well as the sum of the two DS as a function of the feed molar ratio of PBA-thiol to the alkene group; B) Variation of the DS in pentenoates and in maltose groups of HA-maltose as well as the sum of the two DS as a function of the feed molar ratio of PBA-thiol to the alkene group.

Figure 3:
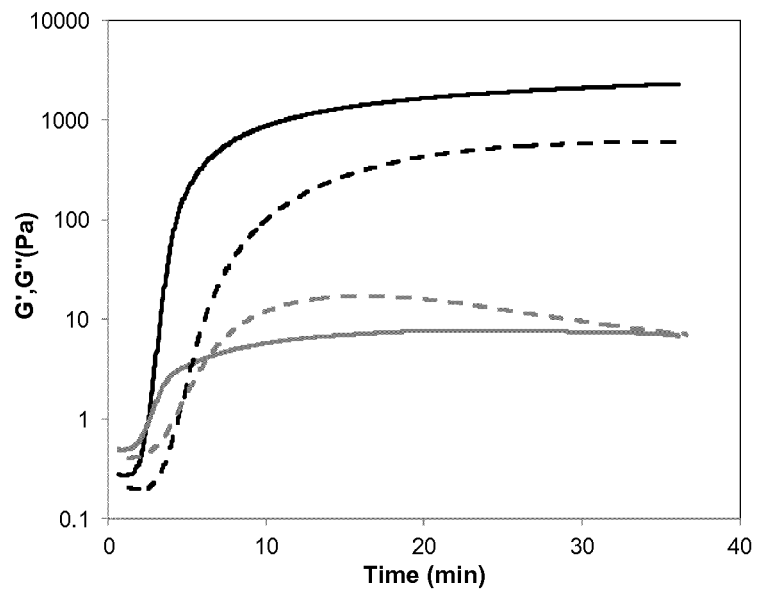
Figure 3:
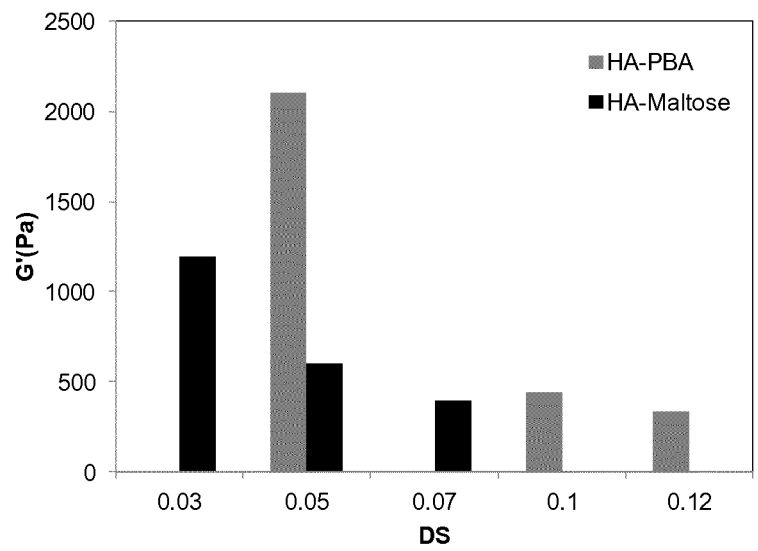

FIG. 3: A) Storage (G', black lines) and loss (G", grey lines) moduli dependence on time of solutions of HA-PBA ($DS_{PBA}$=0.05, $DS_p$=0.29, $C_p$=15 g/L in 0.01 M HEPES, pH 7.4) (continuous lines) and of HA-maltose ($DS_{maltose}$=0.05, $DS_p$=0.29, $C_p$=15 g/L in 0.01 M HEPES, pH 7.4) (dotted lines) in the presence of photoinitiator (0.05% w/v) and PEG-$(SH)_2$ (molar ratio of thiol groups to alkene groups=1). Beginning at t=1 min, the sample was exposed to UV irradiation with 20 mW/cm² intensity (the oscillation frequency was fixed at 1 Hz). B) Comparison of the storage modulus of hydrogels prepared from solutions of HA-PBA and HA-maltose possessing different DS in PBA and maltose, in the presence of photoinitiator (0.05% w/v) and PEG-$SH_2$ (molar ratio of thiol groups to alkene groups=1).

FIG. 4: Comparison of the dynamic rheological behavior of mixtures of HA-PBA/HA-maltose at different PBA/maltose molar ratios, and of solutions of initial HA, HA-PBA, HA-maltose alone. A) Variation of the storage and loss moduli as a function of frequency. B) Variation of the complex viscosity as a function of frequency. The total polymer concentration $C_p$ was fixed at 15 g/L. Solvent: 0.01 M HEPES, pH 7.4; temperature: 25° C.

Figure 5:
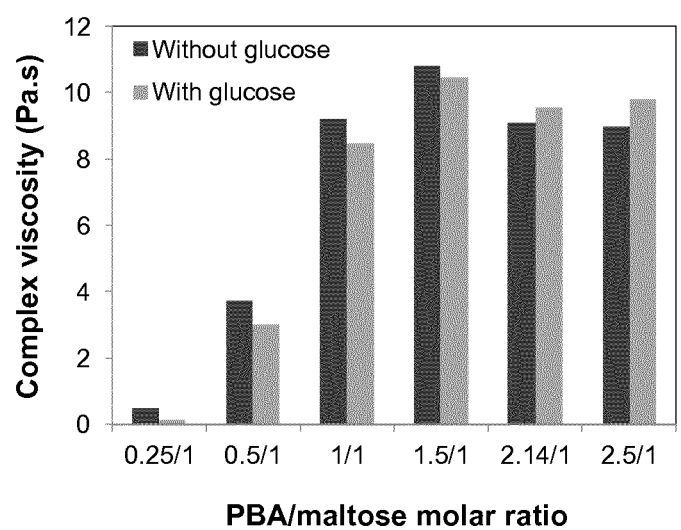
Figure 5:
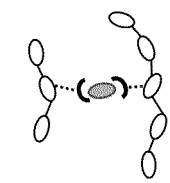
Figure 5:
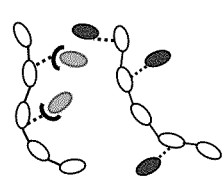

FIG. 5: Effect of addition of glucose on the HA-PBA/HA-maltose mixtures with different [PBA]/[maltose] ratios. A) Comparison of the complex viscosity values at 1 Hz in the absence and in the presence of free glucose (15 mM). The total polymer concentration $C_p$ was fixed at 15 g/L. Solvent: 0.01 M HEPES, pH 7.4; temperature: 25° C. B) Cross-linking of HA chains by free glucose. C) Dissolution of the network upon addition of free glucose, which acts as a competitor of the grafted maltose moiety.

Figure 6:
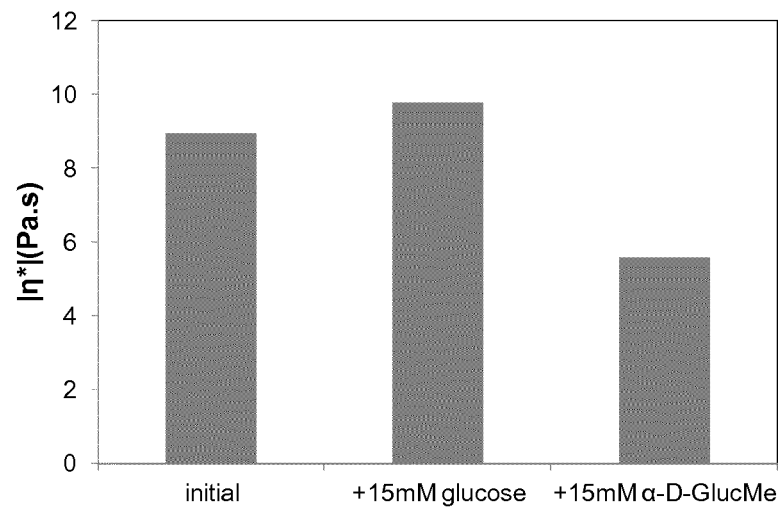
Figure 6:
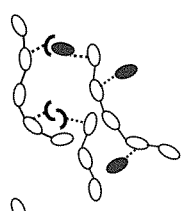
Figure 6:
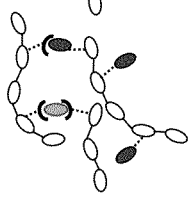
Figure 6:
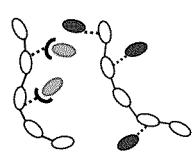

FIG. 6: Comparison of the effect of addition of glucose and α-D-GlucMe at a concentration of 15 mM on the HA-PBA/HA-maltose mixture with the greatest ratio [PBA]/[maltose] (2.5/1). A) complex viscosity values at 1 Hz. The total polymer concentration $C_p$ was fixed at 15 g/L. Solvent: 0.01 M HEPES, pH 7.4; temperature: 25° C. B) Formation of the network by to HA-PBA/HA-maltose complexation. C) Enhancement of the network by free glucose complexation. D) Disruption of the network due to the competitive binding of free glucose to the grafted PBA groups.

Figure 7:
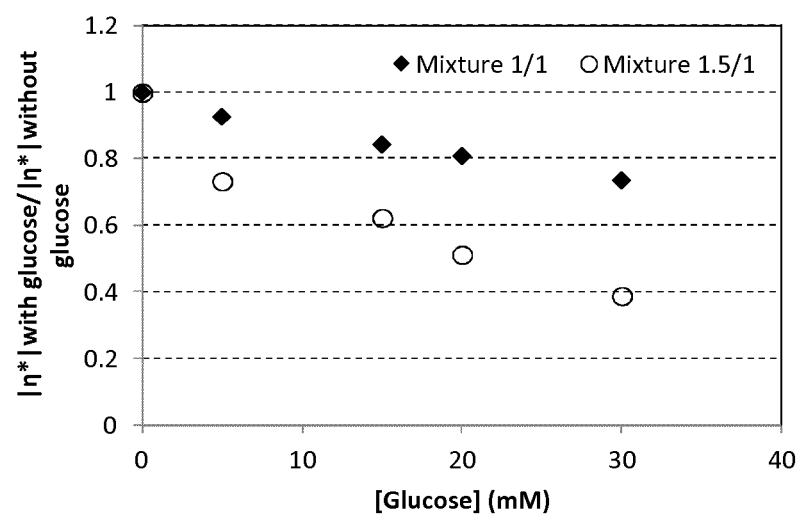

FIG. 7: Variation of $|\eta^*|_{with\ Gluc}/|\eta^*|_{without\ Gluc}$ (values at 1 Hz) as a function of glucose concentration measured from HA-PBA/HA-maltose mixtures with different [PBA]/[maltose] ratios (1/1 and 1.5/1). The total polymer concentration $C_p$ was fixed at 15 g/L. Solvent: 0.01 M HEPES, pH 7.4; temperature: 37° C.

Figure 8:
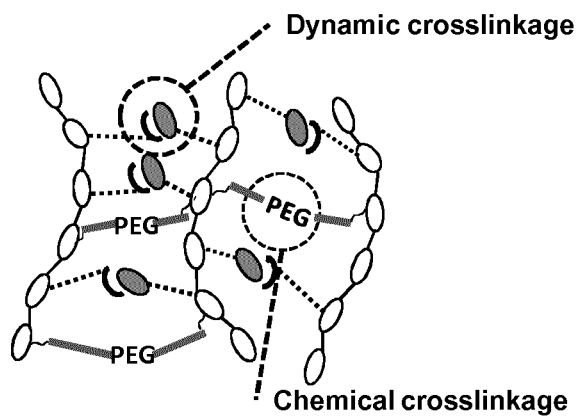
Figure 8:
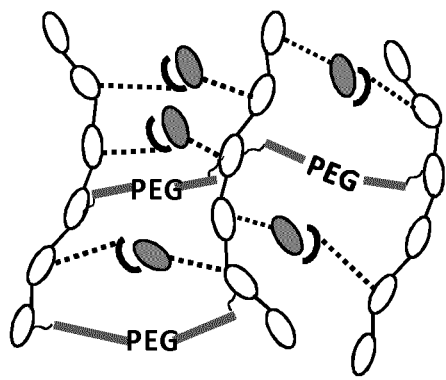

FIG. 8: Doubly crosslinked hydrogel

Figure 9:
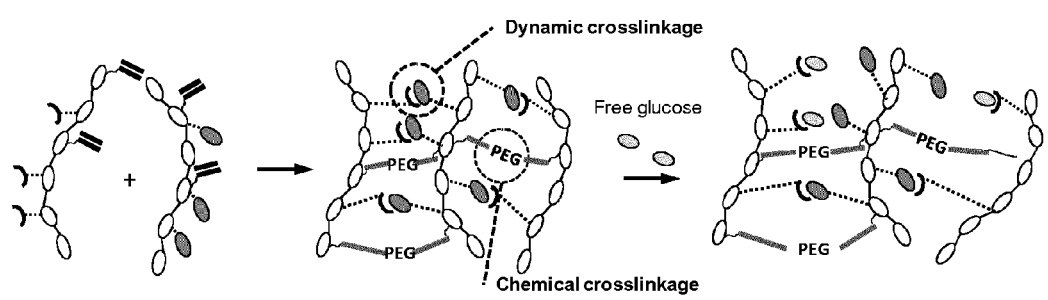

FIG. 9: Formation of doubly crosslinked hydrogel

EXAMPLES

Example 1

Synthesis of the Thiol Precursors

PBA-SH

To a solution of 3-aminophenylboronic acid (APBA, 1 g, 5.4 mmol) in ultrapure water (18 mL) at 4° C., [1-ethyl-3-

(dimethylamino)propyl]carbodiimide hydrochloride (1.24 g, 6.48 mmol) was added. The pH was adjusted to 4.8 using 0.5 M NaOH and the APBA solution was degassed with nitrogen for 20 minutes. Next, mercaptopropionic acid (0.688 mL, 6.48 mmol) which was dissolved in ultrapure water (5 mL) was added dropwise to the APBA solution and the reaction mixture was stirred for 1 h under nitrogen at 4° C. After additional stirring at room temperature under nitrogen for 12 h, the modified APBA was extracted five times with ethyl acetate. After evaporation of the solvent, the residue was purified by recrystallization from water and obtained as a yellow solid in 18% yield (0.215 g, 0.96 mmol).

$^1$H NMR (400 MHz, DMSO-d6) δ (ppm): 7.83 (s, 1H, Ph), 7.70-7.72 (d, 1H, Ph), 7.45-7.47 (d, 1H, Ph), 7.23-7.27 (m, 1H, Ph), 2.71-2.76 (m, 2H, CH$_2$), 2.59-2.63 (m, 2H, CH$_2$).

$^{13}$C NMR (400 MHz, DMSO-d6) δ (ppm): 20.2 (1C, SH—CH$_2$), 39.8 (1C, CH2-C=O), 121.6, 125.7, 128.1 (4C, CH Ph), 129.4 (1C, =C—B Ph), 138.7 (1C, NH—C, Ph), 169.8 (1C, C=O)

Maltose-Cystamine

To an aqueous solution of maltose (0.4 g, 1.111 mmol) in 40 mL ultrapure water at room temperature, O-(carboxymethyl)hydroxylamine hemihydrochloride (0.121 g, 1.111 mmol) was added. The pH was adjusted to 4.8 using 0.5 M NaOH. The reaction mixture was stirred for 24 hours at room temperature and then, was neutralized to pH 7 by addition of 0.5 M NaOH. The maltose-COOH derivative was then recovered by freeze-drying as a white powder in 91% yield (0.421 g, 1.01 mmol). To a solution of maltose-COOH (0,750 g, 1.8 mmol) in dry DMF (75 mL), hydroxybenzotriazole (HOBt) (0,486 g, 3.6 mmol), N,N'-diisopropylcarbodiimide (DIC) (0.909 g, 7.2 mmol) and cystamine (0.203 g, 0.9 mmol) were successively added. The resulting mixture was stirred overnight at room temperature under nitrogen. After evaporation of most of the solvent, the residual syrup was poured dropwise into acetone (500 mL) under stirring. The white precipitate was collected by filtration, washed three times with acetone and dried to give the crude product in 91% yield (778 g, 0.8 mmol) which contained the desired derivative (65%) and initial maltose (35%). Due to the selectivity of the thiol-ene addition used for the synthesis of PBA modified HA, the crude product was used without further purification.

$^1$H NMR (400 MHz, D$_2$O) d (ppm): 7.75 (1H, anomeric Hβ from linked glucose unit, N=CH$_β$—), 7.05 (1H, anomeric Hα from linked glucose unit, N=CH$_α$—), 5.4 (1H, anomeric H from pendant glucose unit), 5.07 (1H, N=CH$_α$, $_β$—CH(OH) from linked glucose group), 4.7 (2H, O—CH$_2$), 4.55 (1H, N=CH$_{α,β}$—CH(OH) from pendant glucose group), 3.5-4.3 (8H, H-3, H-4, H-5, H-6 from linked and pendant glucose groups), 2.9 (2H, NH—CH$_2$—CH$_2$), 2.82 (2H, NH—CH$_2$—CH$_2$).

Example 2

Synthesis of Pentenoate-Modified HA

HA-100 (1 g, 2.5 mmol, M$_w$=100000 g/mol) was dissolved in ultrapure water (50 mL) at 4° C., and the resulting mixture was kept at 4° C. under continuous stirring overnight for complete dissolution. DMF (33 mL) was then added dropwise in order to have a water/DMF ratio of (3/2, v/v). Pentenoic anhydride (0.454 g, 2.5 mmol) was added while maintaining the pH between 8 and 9 (by adding 0.5 M NaOH) for 4 h. The reaction was kept at 4° C. under continuous stirring for one night. After this time, NaCl was added to the reaction mixture to have a NaCl concentration of 0.5 M. The polymer was precipitated by addition of ethanol (with a water/EtOH (v/v) ratio of 2/3). After removal of the supernatant, the precipitate was successively washed with mixtures of water/EtOH (3/7, 1/4, 1/9, v/v) and finally dissolved in ultrapure water for a final purification by diafiltration with ultrapure water. The product was recovered by freeze-drying (1.024 g). The degree of substitution of HA-pentenoate was found to be 0.20±0.01 by $^1$H NMR.

$^1$H NMR (400 MHz, D$_2$O) δ (ppm): 4.55 (H-1 from N-acetylglucosamine unit), 4.25 (H-1 from glucuronic acid), 3.9-3.1 (H-2, H-3, H-4, H-5, H-6 protons of HA), 1.85 (CH$_3$—CO from HA), 5.80 (m, 1H, CH=CH2), 4.98 (m, 2H, CH=CH$_2$), 2.45 (m, 2H, CH$_2$—C=O), 2.29 (m, 2H, OCCH$_2$—CH$_2$).

Example 3

Synthesis of HA-PBA

To a solution of HA-pentenoate in a mixture of water/EtOH (3/2, v/v), in the presence Irgacure 2959 (0.05% w/v) as a photoinitiator, PBA-SH dissolved in 1 ml of EtOH was added. The grafting of PBA-SH moieties was performed under UV radiation (λ=365 nm). The product was purified by diafiltration with ultrapure water and was recovered by freeze-drying (0.298 g). The degree of substitution of HA-PBA was found to be 0.12±0.01 by $^1$H NMR.

$^1$H NMR (400 MHz, D$_2$O) δ (ppm): 4.55 (H-1 from N-acetylglucosamine unit), 4.25 (H-1 from glucuronic acid), 3.9-3.1 (H-2, H-3, H-4, H-5, H-6 protons of HA), 1.85 (CH$_3$—CO from HA), 7.66 (s, 1H, NH—C—CH—C—B from Ph), 7.49 (m, 2H, C—CH—CH—CH—C—B from Ph), 7.37 (m, 1H, C—CH—CH—CH—C—B from Ph), 2.81 (m, 2H, CH2-CO), 2.64 (m, 2H, S—CH2-CH2-CO), 2.53 (m, 2H, CH2-CH2-CH2-S), 1.55 (m, 4H, CH2-CH2-CH2-S).

Example 4

Synthesis of HA-Maltose

The first step consisted in reducing the disulfide bond of maltose-cystamine. Thus, to an aqueous solution of maltose-cystamine (0.2 g, 0.211 mmol) in 4 mL degassed ultrapure water at room temperature, a solution of tris(2-carboxyethyl) phosphine hydrochloride (91 mg, 0.317 mmol) in 1 ml of degassed ultrapure water was added and the pH was adjusted to 5-5.5. The mixture was stirred for 15 min under nitrogen at room temperature to give maltose-SH. The pH was adjusted to 7.4 using 0.1 M NaOH and the solution was added to an aqueous solution of HA-pentenoate in the presence Irgacure 2959 (0.05% w/v) as a photoinitiator. The grafting of maltose-SH moieties was performed under UV radiation (λ=365 nm). The product was purified by diafiltration with ultrapure water and was recovered by freeze-drying (0.148 g). The degree of substitution of HA-maltose was found to be 0.06±0.01 by $^1$H NMR.

$^1$H NMR (400 MHz, D$_2$O) δ$_H$ (ppm) 4.55 (H-1 from N-acetylglucosamine unit), 4.25 (H-1 from glucuronic acid), 3.9-3.1 (H-2, H-3, H-4, H-5, H-6 protons of HA), 1.85 (CH$_3$—CO from HA), 1.52 (m, 2H, CH2-CH2-CH2-S), 1.62 (m, 2H, CH2-CH2-CH2-S), 2.35 (m, 2H, OC—CH$_2$) 2.63 (m, 2H, CH2-CH2-CH2-S), 2.82 (m, 2H, S—CH2-CH2-NH), 7.63 (m, 1H, H anomer of maltose).

Example 5

Formation and Rheological Behavior of the Dynamic Hydrogels

The dynamic hydrogels were formed by mixing aqueous solutions at physiological pH of HA-PBA (DS=0.12) and HA-maltose (DS=0.06). These mixtures lead to the formation of macroscopically transparent "hydrogels" for a total polymer concentration of 15 g/L (~3 times higher than the critical overlap concentration C* (~3.3 g/L) of initial HA) in the presence of salt (0.15 M NaCl). The formation of such networks results from the simultaneous formation of many complexes between the PBA and maltose moieties grafted along the HA chain. Interestingly, cross-linking was observed at physiological pH, which is unusual compared to other polymer complexes involving this boronate derivative which can only stably exist at alkaline pH. More complex chemistry is generally required to achieve boronate-glucose complexation at physiological pH. As represented hereinbelow, PBA derivatives exist in both charged—and also hydrophilic—and uncharged—and relatively hydrophobic—states in aqueous solution. Upon diol addition, it is stated that only the charged state (2) forms a stable complex with diol through reversible covalent bonding whereas the neutral form (1) is highly susceptible to hydrolysis. In the present case, the situation may be different due to the presence on HA of charges and of diol groups in large excess. This may promote the formation of the uncharged trigonal ester form of PBA (3), which may have a large impact on the equilibrium depicted herein below. As discussed previously, the effect of the neutral ester (3) on the equilibrium cannot be ignored in assessing the overall affinity of boronic acid to a particular diol. It has been also reported that the $pK_a$ of the boronate ester of many monosaccharides is 2-4 units lower than that of boronic acid. Consequently, it can be assumed that the grafting of PBA on HA moves the apparent $pK_a$ of PBA closer to the $pK_a$ of the ester, allowing boronate-glucose complexation at physiological pH.

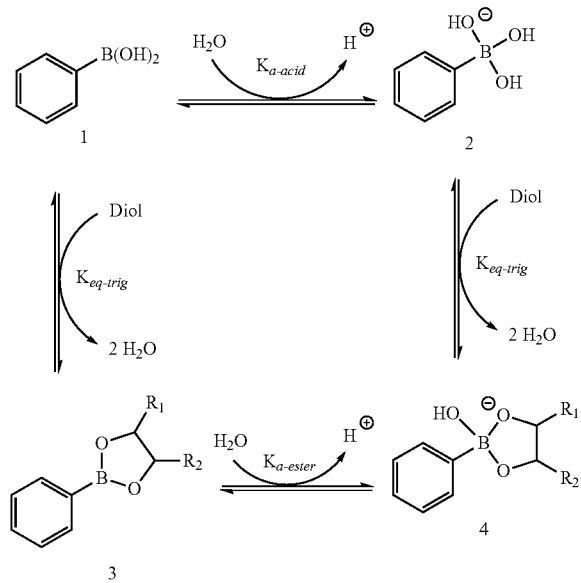

Equilibria of Phenyboronic Acid in Aqueous Solution in the Presence of Diol

Figure 4A:
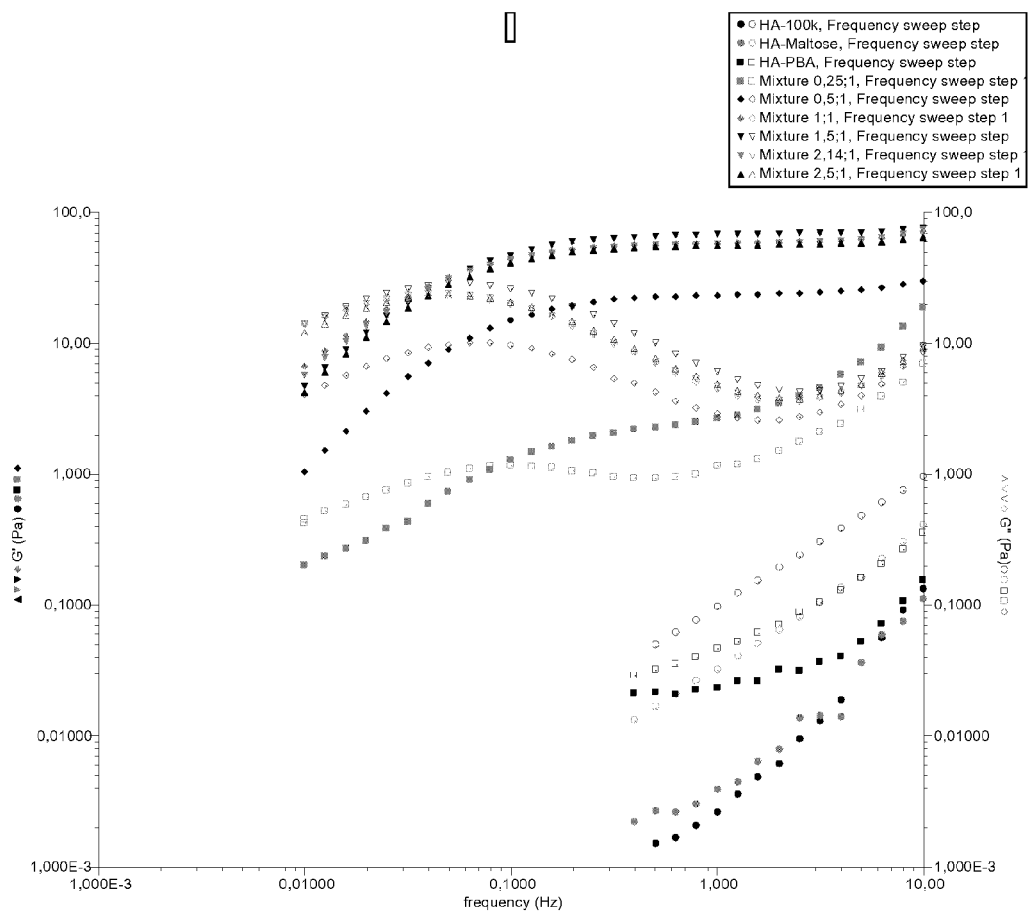
Figure 4B:
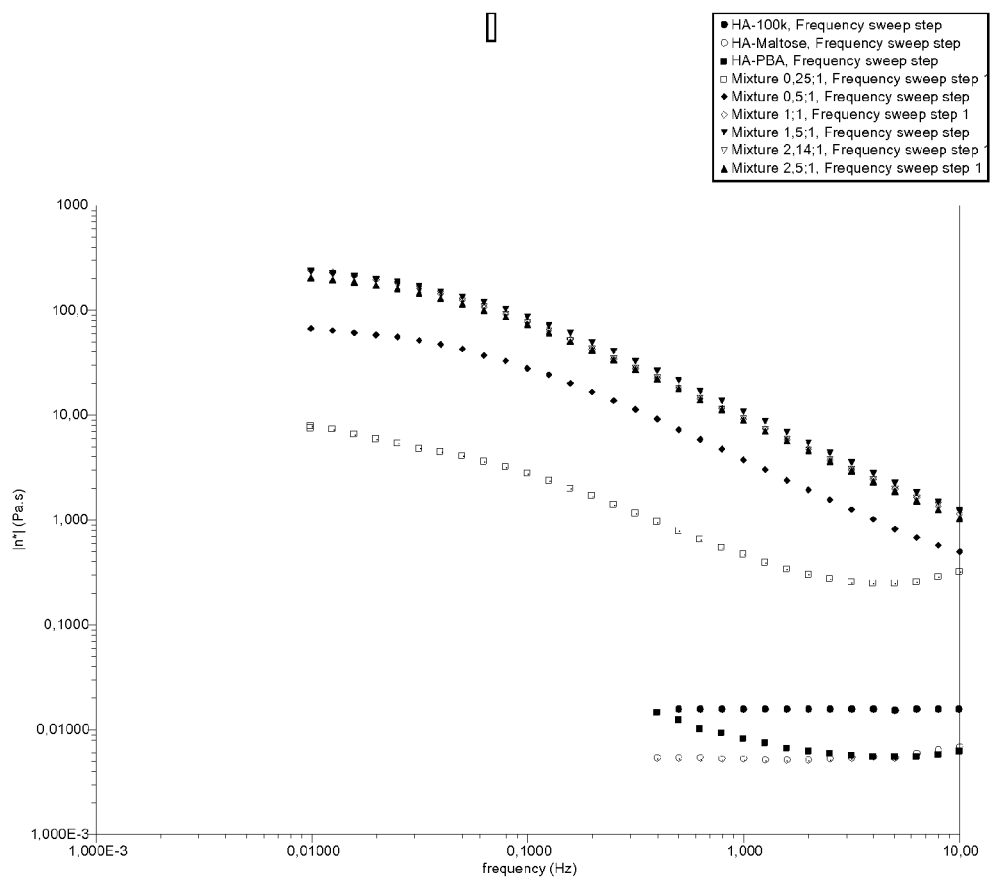

FIG. 4A compares the frequency dependence of the dynamic rheological moduli, G' and G", of HA-PBA/HA-maltose mixtures (total polymer concentration $C_p$=15 g/L) at different PBA/maltose molar ratios ([PBA]/[maltose]=0.5, 1, 1.5, 2.14, 2.5) with that of solutions of initial HA and its derivatives (HA-PBA, HA-maltose) alone ($C_p$=15 g/L). From this figure, it can be observed that the values of the storage and loss moduli for the mixtures are much higher than those obtained for the solutions of HA and its derivatives alone, although the polymer concentration is the same. The elastic modulus increases at least by two orders of magnitude. Moreover, G' is larger than G" within a large range of frequency for the HA-PBA/HA-maltose mixtures, reflecting a viscoelastic behavior, contrary to the solutions of HA, HA-PBA and HA-maltose which exhibit a viscous character (G">G') within the whole range of frequencies covered. These results thus provided evidence of the effective complexation between the grafted PBA and maltose moieties, thus creating a dynamic three-dimensional network. Increasing the amount of PBA with respect to maltose up to a PBA/maltose molar ratio of 1.5 leads to an increase of the elastic modulus (FIG. 4A) and of the complex viscosity (FIG. 4B). Above a PBA/maltose ratio of 1.5, the elastic modulus and the complex viscosity remain constant. This indicates a higher density of effective interchain junctions resulting from the higher probability of PBA/maltose complex formation. Such a result may be related to the fact that PBA can also form cyclic boronic esters with the sugar units of HA, implying that excess PBA with respect to maltose is required for the formation of more stable junction points.

Example 6

Measurement of the Viscosity as a Function of the Amount of Glucose

From these data, the mixtures were expected to be sensitive to the addition of glucose. This was confirmed by measuring the complex viscosity of the mixture as a function of the amount of added glucose (FIG. 5). More importantly, we showed the ability to control the type of the response by simply varying the HA-PBA/HA-maltose ratio. As can be seen from FIG. 5A, addition of glucose at a concentration of 15 mM (corresponding to a high concentration in the blood of diabetics patients, i.e. 3 times the normoglycemia) to the HA-PBA/HA-maltose mixture with the PBA/maltose ratios ranging from 0.25/1 to 1.5/1 results in a decrease of the complex viscosity, indicating that the competitive displacement mechanism between free glucose and terminal glucose moieties on the HA chains is taking place. In contrast, addition of glucose at the same concentration to the mixtures with greater ratios (2.14/1 and 2.5/1) causes an increase of the complex viscosity. It is known that certain monosaccharides can be bound to two boronic acid groups using 1,2-diol and 4,6- or 5,6-diol. D-glucose is one such monosaccharide that has the high bridge-forming ability. Therefore, it can be reasonably assumed that in the latter system, the glucose molecule also acts as a cross-linking agent. In this case, the hydrogel will experience a contraction upon glucose addition. This behavior can also be useful for controlling insulin output in a self-regulating delivery system. Indeed, glucose-sensitive hydrogels can be used for their gating properties after being cast or grafted in the pores of a membrane. The hydrogel contraction increases the membrane permeability as a function of glucose concentration.

Example 7

Competitive Displacement Experiments Using 1-O-Methyl-α-D-Glucopyranoside

This hypothesis was additionally supported by competitive displacement experiments using 1-O-methyl-α-D-glucopyranoside (α-D-GlucMe). Contrary to D-glucose, addition of α-D-GlucMe (at a concentration of 15 mM) to HA-PBA/HA-maltose mixtures with the greatest ratio (2.5/1) lead to a decrease in complex viscosity (FIG. 6A). This result fully supported the hypothesis that D-glucose acts a cross-linking agent.

Example 8

Viscosity Depending on the [PBA]/[Maltose] Ratio

FIG. 7 shows the variation of $|\eta^*|_{with\ Gluc}/|\eta^*|_{without\ Gluc}$, i.e. the ratio of the complex viscosity values obtained at a frequency of 1 Hz of HA-PBA/HA-maltose mixtures with different [PBA]/[maltose] ratios (1/1 and 1.5/1) after and before addition of glucose, with increasing glucose content (5-50 mM). A decrease of viscosity over the 5-50 mM glucose range can be observed for the two mixtures, which confirms the glucose sensitivity of the system. This decrease reflects the loss of cross-linkages, leading to a loosening of the network. Notably, the rate of decrease is different for the two [PBA]/[maltose] ratios, which indicates that the glucose responsiveness of the dynamic network can be easily optimized. This property can be used to control the release of a macromolecule by diffusion through the network. Such hydrogels could be loaded with insulin to achieve its delivery as a function of glycemia variations.

Example 9

Formation of Chemical Hydrogels by Radical-Thiol Ene Additions Reactions

The radical coupling of thiols to pentenoate-modified polysaccharides can be advantageously used to prepare chemical networks with permanent crosslinks. Both HA-PBA and HA-maltose were chemically cross-linked using a bisthiolated poly(ethylene glycol) (PEG-(SH)$_2$, $M_n$=3400 g/mol) as a cross-linker. The photocrosslinking reaction was monitored in situ by photorheometry. FIG. 3A shows the time sweep profiles of the storage modulus (G') and loss modulus (G") obtained from solutions of HA-PBA and HA-maltose with a DS in PBA and maltose of 0.05 ($C_p$=15 g/L in 0.01 M HEPES, pH 7.4 with [NaCl]=0.15 M) in which the photoinitiator Irgacure 2959 and PEG-(SH)$_2$ were added (molar ratio of thiol groups to alkene groups=1). As the two products were prepared from the same HA-pentenoate sample (with a DS of 0.34), the DS of pentenoate groups for both derivatives is 0.29. The sample was equilibrated for 1 min before being illuminated with 20 mW/cm$^2$ UV intensity for a time of 35 min. Initially, G" is larger than G', reflecting the viscous behavior of the sample. After a short induction period following the beginning of UV radiation, the storage modulus increases sharply due to the formation of elastic effective intermolecular cross-links, exceeding the loss modulus. The G' curve levels off at 20 min, indicating the end of the gelation process. In this context, the steady-state value of G' was used as a measure for hydrogel elasticity. FIG. 3B compares the elasticity of hydrogels (G' measured at t=20 min) prepared from solutions of HA-PBA and HA-maltose possessing different DS in PBA and maltose, respectively. As expected, the elasticity decreases as the DS in functional molecules increases (i.e. as the DS in pentenoates decreases). A significant difference in the elasticity can be observed for the hydrogels prepared from HA-PBA and HA-maltose with a DS of 0.05. This may be attributed to the presence of additional crosslinkages resulting from the formation of ester bonds between PBA and sugars of HA.

Example 10

Synthesis of Doubly Cross-Linked Hydrogels Loaded with Insulin

HA-p-PBA (0.0027 g, $DS_p$=0.16 and $DS_{PBA}$=0.14) and HA-p-maltose (0.0033 g, $DS_p$=0.19 and $DS_{maltose}$=0.11) were dissolved separately in 0.01 M HEPES, pH 4 with [NaCl]=0.15 M ([HA-p-PBA]=[HA-p-maltose]=15 g/L). The two solutions are stirred for 1 night at 4° C. The photoinitiator Irgacure 2959 (0.002 g, 0.009 mmol) and PEG-(SH)$_2$ (0.0048 g, 0.0014 mmol, molar ratio of thiol groups to alkene groups=1) are added to the solution of HA-p-PBA under stirring. Next, both solutions (0.250 mL of HA-p-PBA and 0.150 mL of HA-p-maltose) are mixed together ([PBA]/[maltose]=1). The resulting mixture (0.100 mL) is then illuminated with 20 mW/cm$^2$ UV intensity for 5 min, leading to the formation of a chemical gel. The gel disk was immersed in 1 mL of 0.01 M HEPES, pH 4 (with [NaCl]=0.15 M), containing FITC-insulin (5800 MW; monomeric) at a concentration of 1.5 mg/mL. After incubation at 4° C. for 1 h, the pH was adjusted to 7.4 by addition of aqueous NaOH (0.1 M) and the disk was immersed in 50 mL of 0.01 M HEPES, pH 7.4 with [NaCl]=0.15 M (termed "HEPES buffer"). The incorporation of FITC-insulin inside the doubly cross-linked hydrogel was demonstrated by fluorescence microscopy.

REFERENCES

WO2012/066133

Wu et al., Chemical Reviews, 111:7855-7875, 2011

Kataoka K, Miyazaki H, Bunya M, Okano T, Sakurai Y. Totally Synthetic Polymer Gels Responding to External Glucose Concentration: Their Preparation and Application to On-Off Regulation of Insulin Release. Journal of the American Chemical Society. 1998; 120:12694-5.

Ravaine V, Ancla C, Catargi B. Chemically controlled closed-loop insulin delivery. Journal of Controlled Release. 2008; 132:2-11.

Samoei G K, Wang W, Escobedo J O, Xu X, Schneider H-J, Cook R L, et al. A chemomechanical polymer that functions in blood plasma with high glucose selectivity. Angewandte Chemie, International Edition. 2006; 45:5319-22.

Wang L, Liu M-Z, Gao C-M, Ma L-W, Cui D-P. A pH-, thermo-, and glucose-, triple-responsive hydrogels: Synthesis and controlled drug delivery. Reactive & Functional Polymers. 2010; 70:159-67.

Wu Z, Zhang S, Zhang X, Shu S, Chu T, Yu D. Phenylboronic acid grafted chitosan as a glucose-sensitive vehicle for controlled insulin release. Journal of Pharmaceutical Sciences. 2011; 100:2278-86.

Ivanov A E, Larsson H, Galaev I Y, Mattiasson B. Synthesis of boronate-containing copolymers of N,N-dimethylacrylamide, their interaction with poly(vinyl alcohol) and rheological behaviour of the gels. Polymer. 2004; 45:2495-505.

Kitano S, Koyama Y, Kataoka K, Okano T, Sakurai Y. A novel drug delivery system utilizing a glucose responsive polymer complex between poly(vinyl alcohol) and poly (N-vinyl-2-pyrrolidone) with a phenylboronic acid moiety. Journal of Controlled Release. 1992; 19:161-70.

Matsumoto A, Yoshida R, Kataoka K. Glucose-responsive polymer gel bearing phenylborate derivative as a glucose-sensing moiety operating at the physiological pH. Biomacromolecules. 2004; 5:1038-45.

The invention claimed is:

1. A polymer composition comprising a mixture of:
    a) Phenyl boronic acid (PBA) modified hyaluronic acid (HA) polymer grafted on at least a hydroxyl with a group comprising phenylboronic acid, wherein said group is selected in the group consisting of phenylboronic acid, 3-aminophenylboronic acid, 4-aminophenylboronic acid, 4-(aminoethylcarbamoyl)-3-fluorophenylboronic acid and 4-[(2-aminoethyl) carbamoyl] phenylboronic acid, and
    b) Cis-diol modified hyaluronic acid (HA) polymer grafted on at least a hydroxyl with a group comprising a cis-diol, wherein said cis-diol is selected in the group consisting of: disaccharides, hexoses, uronic acid derivatives of hexoses, hexosamines, N-acetyl derivatives of hexosamines, glycerol, mannitol and sialic acid.

2. The polymer composition according to claim 1, wherein the composition has a pH from 7 to 10.

3. The polymer composition according to claim 1, wherein the composition has a pH from 7 to 7.5.

4. The polymer composition according to claim 1, wherein the PBA modified HA polymer is further grafted on at least a hydroxyl with an alkene group and the cis-diol modified HA polymer is further grafted on at least a hydroxyl with an alkene group.

5. The polymer composition according to claim 4, wherein the alkene group is selected in the group consisting of pentenoate and maleimide.

6. The polymer composition according to claim 1, wherein the PBA modified HA polymer and the cis-diol modified HA polymer are reversibly covalently crosslinked via their groups comprising phenylboronic acid and their groups comprising a cis-diol.

7. The polymer composition according to claim 4, wherein the PBA modified HA polymer and the cis-diol modified HA polymer are chemically crosslinked via their alkene groups and are further reversibly covalently crosslinked via their groups comprising phenyl boronic acid and their groups comprising a cis-diol.

8. An injectable hydrogel comprising a polymer composition according to claim 6.

9. An implantable hydrogel comprising a polymer composition according to claim 7.

10. A drug delivery system comprising a polymer composition according to claim 1 and a drug contained in said polymer composition.

11. A drug delivery system according to claim 10 wherein the drug is insulin.

12. A method for treating diabetes mellitus implanting the drug delivery system of claim 10.

13. A process for manufacturing a reversibly crosslinked hydrogel comprising a HA polymer composition comprising the steps of:
    a) Preparing a phenyl boronic acid (PBA) modified hyaluronic acid (HA) polymer grafted on at least a hydroxyl with a group comprising phenylboronic acid, wherein said group is selected in the group consisting of phenylboronic acid, 3-aminophenylboronic acid, 4-aminophenylboronic acid, 4-(aminoethylcarbamoyl)-3-fluorophenylboronic acid and 4-[(2-aminoethyl) carbamoyl] phenylboronic acid;
    b) Preparing a cis-diol modified hyaluronic acid (HA) polymer grafted on a hydroxyl with a group comprising a cis-diol, wherein said cis-diol is selected in the group consisting of: disaccharides, hexoses, uronic acid derivatives of hexoses, hexosamines, N-acetyl derivatives of hexosamines, glycerol, mannitol and sialic acid;
    c) Mixing aqueous solutions of the PBA modified HA polymer of step a) and of the cis-diol modified HA polymer of step b) at a pH comprised between 7 and 10, to obtain a reversibly crosslinked hydrogel.

14. The process for manufacturing a hydrogel according to claim 13 wherein in step c) mixing aqueous solutions of the PBA modified HA polymer of step a) and of the cis-diol HA polymer of step b) is performed at a pH comprised between 7.2 and 9.5.

15. The process for manufacturing a hydrogel according to claim 13 wherein in step c) mixing aqueous solutions of the PBA modified HA polymer of step a) and of the cis-diol HA polymer of step b) is performed in the presence of a drug thereby incorporating the drug into the HA polymer composition.

16. A process for manufacturing a double cross-linked hydrogel comprising a hyaluronic acid (HA) polymer composition comprising the steps of:
    a) Preparing a phenyl boronic acid (PBA) modified hyaluronic acid (HA) polymer grafted on at least a hydroxyl with a group comprising phenylboronic acid, wherein said group is selected in the group consisting of phenylboronic acid, 3-aminophenylboronic acid, 4-aminophenylboronic acid, 4-(aminoethylcarbamoyl)-3-fluorophenylboronic acid and 4-[(2-aminoethyl) carbamoyl] phenylboronic acid, and grafted on at least a hydroxyl with an alkene group;
    b) Preparing a cis-diol modified hyaluronic acid (HA) polymer grafted on a hydroxyl with a group comprising a cis-diol, wherein said cis-diol is selected in the group consisting of: disaccharides, hexoses, uronic acid derivatives of hexoses, hexosamines, N-acetyl derivatives of hexosamines, glycerol, mannitol and sialic acid, and
    grafted on at least a hydroxyl with an alkene group;
    c) Mixing aqueous solutions of the PBA modified HA polymer of step a) and of the cis-diol modified HA polymer of step b) at a pH from 3 to 6.5 to obtain a HA polymer composition;
    d) Photocrosslinking of the HA polymer composition obtained in step c) by the radical addition of PEG-$(SH)_2$ on the alkene groups on the HA polymer composition to obtain a chemically crosslinked HA polymer composition;
    e) Crosslinking of the HA polymer composition of step d) at a pH comprised between 7 and 10.

17. The process for manufacturing a double cross-linked hydrogel comprising a polymer composition according to claim 16 wherein after step d) a drug is incorporated into the HA polymer composition.

18. The process for manufacturing a double cross-linked hydrogel comprising a polymer composition according to claim 16 wherein after step e) crosslinking of the HA composition of step d) is performed at a pH comprised between 7.2 and 9.5.

19. A method for treating diabetes mellitus implanting the drug delivery system of claim 11.

\* \* \* \* \*